(12) United States Patent
Lou et al.

(10) Patent No.: US 9,636,074 B2
(45) Date of Patent: May 2, 2017

(54) CALCULATING THE MOTION VECTOR FIELD FOR A RECONSTRUCTED CT SCAN IMAGE

(71) Applicant: Shenyang Neusoft Medical Systems Co., Ltd., Shenyang (CN)

(72) Inventors: Shanshan Lou, Shenyang (CN); Han Zheng, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 85 days.

(21) Appl. No.: 14/918,594

(22) Filed: Oct. 21, 2015

(65) Prior Publication Data

US 2016/0110864 A1    Apr. 21, 2016

(30) Foreign Application Priority Data

Oct. 21, 2014   (CN) .......................... 2014 1 0562662
Oct. 19, 2015   (CN) .......................... 2015 1 0683484

(51) Int. Cl.
*A61B 6/00* (2006.01)
*A61B 6/03* (2006.01)
*G06T 11/00* (2006.01)
*G06T 7/246* (2017.01)

(52) U.S. Cl.
CPC .............. *A61B 6/504* (2013.01); *A61B 6/032* (2013.01); *A61B 6/469* (2013.01); *A61B 6/5264* (2013.01); *G06T 7/246* (2017.01); *G06T 11/008* (2013.01); *A61B 6/481* (2013.01); *G06T 2207/10081* (2013.01); *G06T 2207/20104* (2013.01); *G06T 2207/30048* (2013.01); *G06T 2207/30101* (2013.01); *G06T 2211/412* (2013.01)

(58) Field of Classification Search
None
See application file for complete search history.

(56) References Cited

U.S. PATENT DOCUMENTS 9,427,200 B2 *  8/2016  Kyriakou ............... A61B 6/503
9,542,762 B2 *  1/2017  Okamoto ............... A61B 6/032
2009/0149741 A1  6/2009  Heigl
(Continued)

FOREIGN PATENT DOCUMENTS

CN    101028196 A    9/2007
CN    101313334 A    11/2008
(Continued)

*Primary Examiner* — Sumati Lefkowitz
*Assistant Examiner* — Jiangeng Sun
(74) *Attorney, Agent, or Firm* — Kilpatrick Townsend & Stockton LLP

(57) ABSTRACT

A method for calculating a motion vector field (MVF) in a reconstructed CT scan image, comprises: determining a region of interest (ROI) based on a vessel centreline in a first reconstructed CT scan image, wherein a motion vector field (MVF) for the ROI is to be calculated; determining at least two time control points for calculating the MVF; calculating a motion level factor of the ROI; calculating motion amounts of the MVF corresponding to each of the time control points; determining the direction of the MVF of the ROI; and calculating the MVF of the ROI according to the motion level factor, the motion amounts of the MVF corresponding to each of the time control points and the direction of the MVF.

18 Claims, 5 Drawing Sheets

(56) References Cited

U.S. PATENT DOCUMENTS

| | | | |
|---|---|---|---|
| 2013/0077843 A1 | 3/2013 | Bruder | |
| 2013/0303884 A1* | 11/2013 | Kuntz | G06T 11/006 |
| | | | 600/417 |
| 2015/0063534 A1* | 3/2015 | Allmendinger | A61B 6/032 |
| | | | 378/19 |
| 2015/0243045 A1* | 8/2015 | Ra | G06T 7/0024 |
| | | | 382/131 |
| 2016/0210741 A1* | 7/2016 | Brendel | G06T 11/006 |
| 2016/0310090 A1* | 10/2016 | Klinder | G06T 7/11 |

FOREIGN PATENT DOCUMENTS

| | | |
|---|---|---|
| JP | 2009160221 A | 7/2009 |
| JP | 2012061019 A | 3/2012 |
| WO | 2004081877 A1 | 9/2004 |

\* cited by examiner

CALCULATING THE MOTION VECTOR FIELD FOR A RECONSTRUCTED CT SCAN IMAGE

The present application claims the priority to Chinese Patent Applications No. 201410562662.8, titled "CALCULATING MOTION VECTOR FIELD FOR A RECONSTRUCTED CT SCAN IMAGE", filed with the Chinese State Intellectual Property Office on Oct. 21, 2014, and another Chinese Patent Applications filed with the Chinese State Intellectual Property Office on Oct. 19, 2015, application number not assigned yet, both of which are incorporated herein by reference in their entireties.

BACKGROUND

Computed Tomography (CT) is a technology for performing continuous slice scanning with an X-ray beam and a detector around a certain region of a subject (e.g., the patient). A CT scanner can be used for diagnosing and investigating various diseases, because of short scanning time and clear images.

CT cardiac scanning is one of the most common applications for CT. After having been perfused with a contrast medium, the heart of a subject is scanned by a CT scanner under guidance of electrocardiogram of the subject, and then an image of the heart is reconstructed based on the acquired scanning data with reconstruction algorithm.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, magnetic resonance imaging (MRI), digital X-ray machine, ultrasound, Positron Emission Tomography (PET), linear accelerator (LINAC), and biochemistry analyzer. Currently, NMS' products are exported to over 60 countries and regions around the globe, serving more than 5,000 renowned customers. NMS's latest successful developments, such as 128 multi-slice CT scanner system, superconducting MRI, linear accelerator, and PET products, have led China to become a global high-end medical equipment producer. As an integrated supplier with extensive experience in large medical equipment, NMS has committed to the study of avoiding secondary potential harm caused by excessive X-ray irradiation to the subject during the CT scanning process.

BRIEF DESCRIPTION OF DRAWINGS

Features of the present disclosure are illustrated by way of example and not limited in the following figures, in which like numerals indicate like elements, in which.

DETAILED DESCRIPTION

The present invention is direct to CT scanning techniques.

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

Theoretically, in order to completely reconstruct a CT scan image, it is necessary to provide a projection angle range of at least $\pi+\gamma$ ($\gamma$ is the sector angle of the fan-shaped or cone-shaped X-ray beam). Meanwhile, within the fixed projection angle range, an image of higher temporal resolution can be reconstructed with a higher rotation speed of gantry. The improvement of mechanical speed, however, is limited, so it may be necessary to calculate the motion vector field (MVF) in a reconstructed CT scan image, and to perform a motion compensated reconstruction to obtain an image with higher time resolution and less motion artefacts.

In order to better understand the primary realization principle of the present disclosure, relevant theory and formulae in the present disclosure are described first.

In an example, assuming that there is a certain motion $\vec{\tau}$ in the coronary vessels of the scanned subject, since projection data collected in different times falls in different ranges corresponding to different time control points, a motion vector (a motion has both magnitude and direction) of the motion $\vec{\tau}$ in each time control point can be calculated on the basis of the projection data, and a complete MVF of the motion $\vec{\tau}$ can be obtained on the basis of the motion vectors in all the time control points. During a motion compensated reconstruction, location parameters of a reconstructed point are superimposed with the calculated motion vector in each time control point, so as to reconstruct the motion compensated image in each time control point.

Besides, since the possible directions of the motion in the coronary vessels may be exhaustive, it is possible to estimate a MVF in each possible direction and select the possible direction corresponding to the minimum motion artefact on the region of interest (ROI) as the ultimate direction of the MVF.

Figure 1:
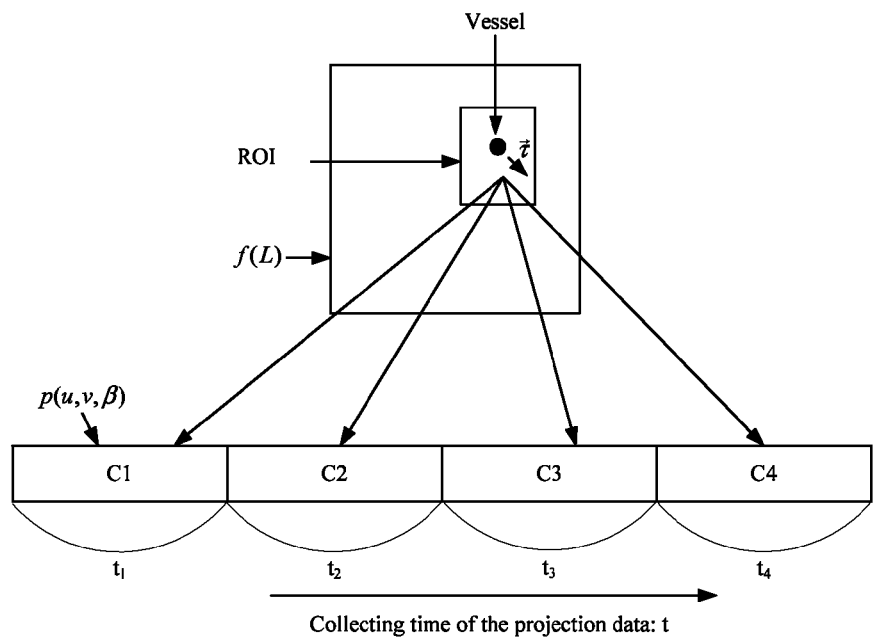
FIG. 1 schematically illustrates a primary principle of a motion vector field (MVF) according to an example of the present disclosure.

FIG. 1 illustrates a primary principle of a MVF according to an example of the present disclosure. In FIG. 1, a reconstructed CT scan image f(L) includes a coronary vessel, and so a ROI, for which a MVF is to be calculated, may be defined based on the centreline of the coronary vessel. The projection parameters of each point in the space may be are calculated as shown in FIG. 2, and FIG. 2 illustrates the primary principle of the MVF according to another example of the present disclosure.

Figure 2:
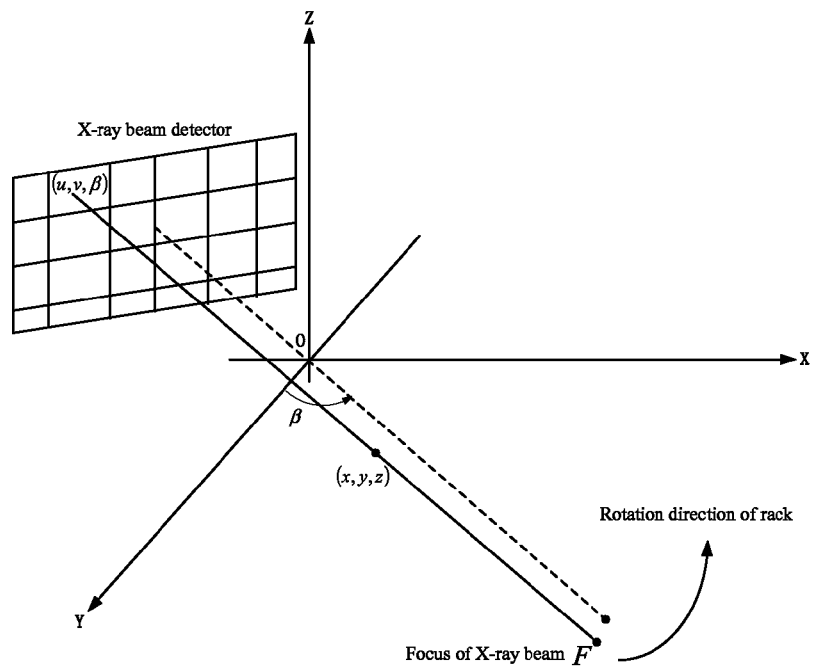
FIG. 2 schematically illustrating the primary principle of the MVF according to another example of the present disclosure.

FIG. 2 illustrates the relationship between the projection parameters and the reconstructed point. The reconstructed CT scan image f(L) and projection data p (e.g. parallel beam projection) may have a relationship shown as Formula 1 and Formula 2:

$$f(x, y, z, c) = \sum p(\beta, B(\beta, M(t_\beta, z, x, y, c_{t\beta,x,y}))) \quad \text{Formula 1}$$

$$B = \quad \text{Formula 2}$$

$$\begin{cases} u = -\sin(\beta)y + \cos(\beta)x \\ v = z + \dfrac{\sin(\beta)x + \cos(\beta)y}{\sqrt{R^2 - (-\sin(\beta)y + \cos(\beta)x)^2}} - (\sin(\beta)x + \cos(\beta)y) \end{cases}$$

wherein, x,y,z are coordinates of the reconstructed point on the reconstructed CT scan image f(L); c is the MVF on the reconstructed point; β is the projection angle, i.e., the intersection angle for a line linking the focus F of X-ray source and the scan centre O with respect to the Y-axis; B is the coordinate of X-ray detector; $M(t,x,y,c_{t,x,y})$ are corrected coordinates of the reconstructed point; u,v are parameters regarding channel and slice direction of the X-ray detector; and R is the rotation radius, i.e., the length of the line linking the focus F and the scan center O.

Since the projection data of different angles are obtained at different scanning times, the collecting time of the projection data at projection angle β can be represented as $t_\beta$. For easy comprehension, in this example, the MVF of 2-dimension plane is calculated, and the motion amount in the Z-axis direction is omitted. It should be understood that, the calculation method for the Z-axis direction may be the same or substantially similar as for the X-axis direction or the Y-axis direction, which are not be repeated here. Such, the coordinates of the reconstructed point after corrected with the motion vector at time t may be shown as Formula 3.

$$M(t, x, y, c_{t,x,y}) = \begin{cases} x + c_{t,x} \\ y + c_{t,y} \end{cases} \quad \text{Formula 3}$$

wherein, $M(t,x,y,c_{t,x,y})$ are corrected coordinates value of the reconstructed point, $c_{t,x}$ is the X-axis projection value of the motion vector at time t, and $c_{t,y}$ is the Y-axis projection value of the motion vector at time t.

Besides, the vessel motion $\vec{\tau}$ in the ROI can be resolved into motions of the projection data at different times, just as shown by Formula 4:

$$\vec{\tau} = \eta \times \phi \quad \text{Formula 4}$$

wherein, η represents the motion direction, φ is a motion level factor indicating movement intensity. In other words, the more intense the motion $\vec{\tau}$ is, the greater the motion level factor φ is, and the more serious the motion artefact on the reconstructed image is; whereas, the milder the motion $\vec{\tau}$ is, the less the motion level factor φ is.

Then, the derivative of motion $\vec{\tau}$ on the reconstructed CT scan image f(L) with respect to the MVF may be calculated through Formula 5 as a MVF derivative:

$$\frac{\partial \vec{\tau}}{\partial c} = \frac{\partial f(L, \vec{\tau})}{\partial c} = \sum_\beta \left( \frac{\partial p}{\partial B} \frac{\partial B}{\partial M} \right) \frac{\partial M(t_\beta, x, y, c_{t_\beta,x,y})}{\partial c} \quad \text{Formula 5}$$

Then, Formula 5 is substituted with Formula 1 and Formula 2, and the MVF derivative corresponding to the collecting time $t_\beta$ may be calculated through Formula 6 and Formula 7:

$$\frac{\partial \vec{\tau}}{\partial x_{t_\beta}} = \sum_\beta \left( \frac{\partial p}{\partial u} \frac{\partial u}{\partial x} + \frac{\partial p}{\partial v} \frac{\partial v}{\partial x} \right) \times \frac{\partial M(t_\beta, x, y, c_{t_\beta,x,y})}{\partial x} \quad \text{Formula 6}$$

$$\frac{\partial \vec{\tau}}{\partial y_{t_\beta}} = \sum_\beta \left( \frac{\partial p}{\partial u} \frac{\partial u}{\partial y} + \frac{\partial p}{\partial v} \frac{\partial v}{\partial y} \right) \times \frac{\partial M(t_\beta, x, y, c_{t_\beta,x,y})}{\partial y} \quad \text{Formula 7}$$

It can be found that, the MVF derivative is a factor related to the reconstruction location (x,y), the projection data p, and the projection angle β. Meanwhile, since the projection angle β is related to the collecting time $t_\beta$, it is assumed that the collecting time $t_\beta$ is within the range of the time control point $t_n$, the motion amount at the time control point $t_n$ can be presented as the sum of the derivative of all the projection data whose collecting time is within the range of the time control point with respect to the MVF. Therefore, the motion amount corresponding to the time control point $t_n$, can be calculated through Formula 8 and Formula 9.

$$c'_{t_n,x} = \quad \text{Formula 8}$$

$$\frac{\partial \vec{\tau}}{\partial x_{t_n}} = \sum_{t_\beta \in t_n} \left( \frac{\partial p}{\partial u} \frac{\partial u}{\partial x} + \frac{\partial p}{\partial v} \frac{\partial v}{\partial x} \right) \times \frac{\partial M(t_\beta, x, y, c_{t_\beta,x,y})}{\partial x}$$

$$c'_{t_n,y} = \quad \text{Formula 9}$$

$$\frac{\partial \vec{\tau}}{\partial y_{t_n}} = \sum_{t_\beta \in t_n} \left( \frac{\partial p}{\partial u} \frac{\partial u}{\partial y} + \frac{\partial p}{\partial v} \frac{\partial v}{\partial y} \right) \times \frac{\partial M(t_\beta, x, y, c_{t_\beta,x,y})}{\partial y}$$

wherein $c'_{t_n,x}, c'_{t_n,y}$ are the motion amounts corresponding to the time control point $t_n$, i.e., the magnitude of the MVF without considering the direction and intensity of the motion. Formula 8 and Formula 9 are substituted with Formula 4, i.e., the direction and the motion level factor are further considered, and then the motion vector corresponding to the time control point $t_n$ can be calculated through Formula 10 and Formula 11.

$$c_{t_n,x} = \eta \times \varphi \times c'_{t_n,x} = \quad \text{Formula 10}$$

$$\eta \times \varphi \times \sum_{t_\beta \in t_n} \left( \frac{\partial p}{\partial u} \frac{\partial u}{\partial x} + \frac{\partial p}{\partial v} \frac{\partial v}{\partial x} \right) \times \frac{\partial M(t_\beta, x, y, c_{t_\beta,x,y})}{\partial x}$$

$$c_{t_n,y} = \eta \times \varphi \times c'_{t_n,y} = \quad \text{Formula 11}$$

$$\eta \times \varphi \times \sum_{t_\beta \in t_n} \left( \frac{\partial p}{\partial u} \frac{\partial u}{\partial y} + \frac{\partial p}{\partial v} \frac{\partial v}{\partial y} \right) \times \frac{\partial M(t_\beta, x, y, c_{t_\beta,x,y})}{\partial y}$$

Besides, since the motion level factor on the basis of image artefact level may not be able to precisely reflect the intensity of vessel motion, an extension factor ω may be introduced to adjust the MVF for obtaining a more accurate MVF and a better reconstruction result. Such, the ultimate MV corresponding to the time control point $t_n$ can be calculated through Formula 12 and Formula 13:

$$C_{t_n,x} = \omega \times c_{t_n,x} \qquad \text{Formula 12}$$

$$C_{t_n,y} = \omega \times c_{t_n,y} \qquad \text{Formula 13}$$

$(C_{t_n,x}, C_{t_n,y})$ is the ultimate motion vector corresponding to the time control points $t_n$; the extension factor $\omega$ is a regulatory factor used to adjust the MVF.

Figure 3:
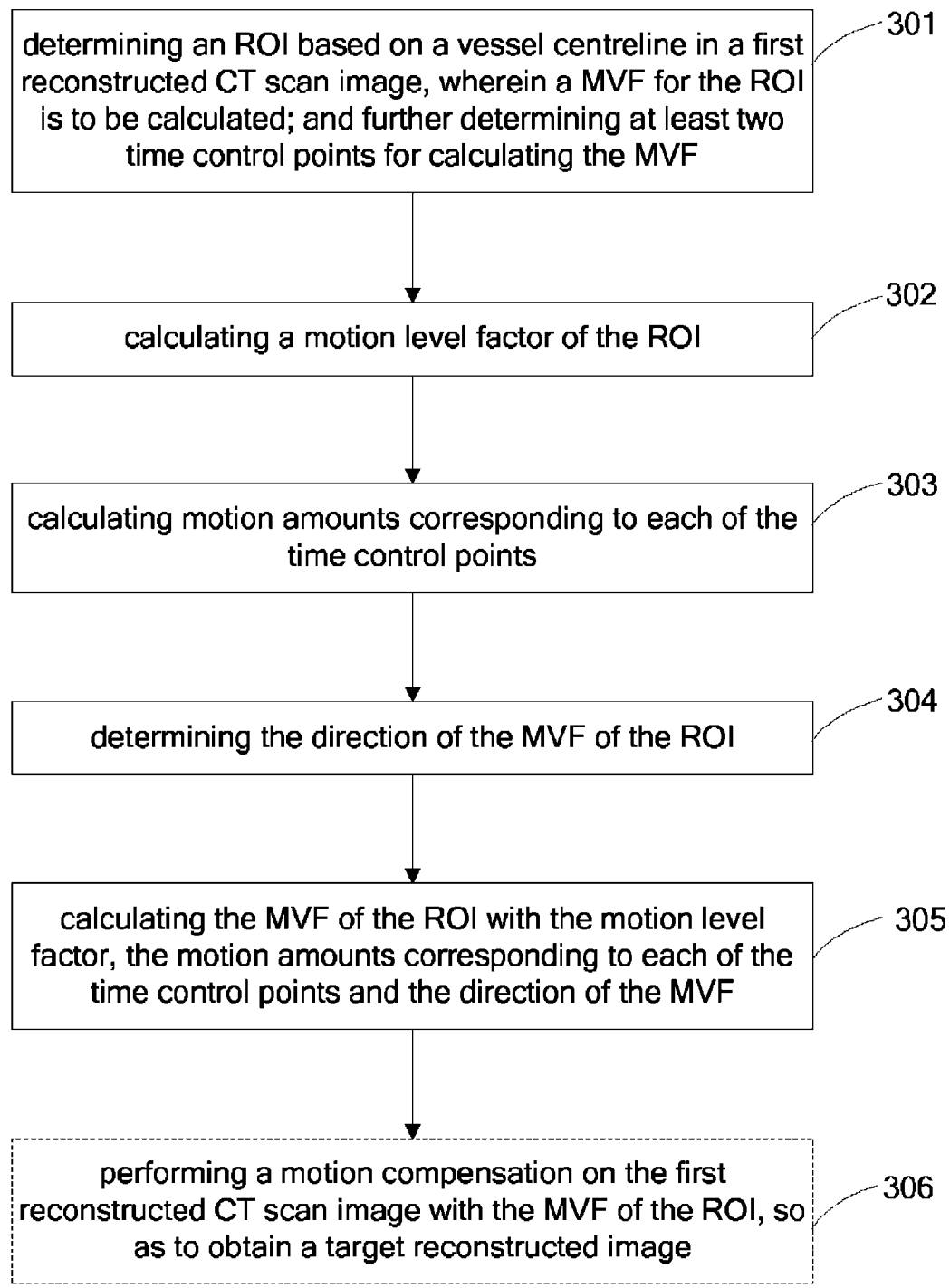
FIG. 3 is a schematic flowchart illustrating a method for calculating the MVF in a reconstructed CT scan image according to an example of the present disclosure.

After an introduction of the primary realization principle of the present disclosure, FIG. 3 illustrates an example of a method for calculating the motion vector field (MVF) in a reconstructed CT scan image, and the method comprises:

Block 301: determining a region of interest (ROI) based on the vessel centreline in a first reconstructed CT scan image, wherein a motion vector field (MVF) for the ROI is to be calculated; and further determining a time control point for calculating the MVF.

Firstly, the ROI of which the MVF is to be calculated may be determined according to the vessel centreline in the first reconstructed CT scan image. It should be understood that the ROI in this example may be singular or multiple, and the size of each ROI may be set by the user according to practical requirements and application scenarios. For example, if the ROI is extended to the whole image, the MVF of the whole image will be calculated. Besides, in this example, the MVF is calculated with respect to some reconstructed point which takes the coronary vessel centreline as centre (referred to as space control point hereafter), the MVF of the locations other than the reconstructed point can be obtained by weighted operation on the MVF of the reconstructed point. It should be understood that, space control point can be singular or multiple, meanwhile the calculation method is consistent among the MVF of each of the space control points, therefore it will be described in detail with an example of a single space control point hereafter.

Generally, the more the number of the time control points is, the more precisely the MVF may be calculated. In a fixed a projection angle range, however, overly concentrated time control points may cause the projection data belonging to a single time control point to be relatively few, so the calculation accuracy of the motion vector on the single time control point might be influenced. So, it may be preferable to choose 5~10 time control points. After fixing the number of the time control points, the range of the projection data corresponding to each of the time control points may be determined according to the projection angle of the acquired projection data.

Block 302: calculating a motion level factor of the ROI.

According to an example, when calculating the motion level factor of the ROI, it may include:

Block A1: calculating the edge gradient standard deviation of the ROI.

For the scanned subject, the motion of the heart blurs the reconstructed CT scan image. Generally, the more the motion artefact is, the more blurred the image is. According to such principle, the absolute value of the edge gradient of the ROI can be calculated through Formula 14:

$$E(a,b) = \frac{|f(a,b) - f(a+1,b)|}{\Delta x} + \frac{|f(a,b) - f(a,b+1)|}{\Delta y} \qquad \text{Formula 14}$$

wherein, $\Delta x$ is the pixel sampling interval on the X-axis, and $\Delta y$ is the pixel sampling interval on the Y-axis; E(a,b) is the absolute value of the edge gradient on the pixel (a,b), a is the X-axis index of the pixel (a,b), and b is the Y-axis index of the pixel (a,b); f(a,b) is the value of the pixel (a,b) on the reconstructed CT scan image.

Then, according to the concept of standard deviation, the edge gradient standard deviation StdE may be calculated with the absolute value of the edge gradient E(a,b). The larger the edge gradient standard deviation StdE is, the sharper the image edge of the ROI is, i.e., the less the motion artefact is. It is possible to determine whether the motion compensated result is good or bad according to the edge gradient standard deviation StdE.

Block A2: determining the motion level factor $\phi$ according to the edge gradient standard deviation StdE.

According to an example, the motion level factor $\phi$ may be calculated using Formula 15:

$$\varphi = \begin{cases} 0 & StdE \geq \varphi_{Th} \\ \varphi_{Th} - StdE & StdE < \varphi_{Th} \end{cases} \qquad \text{Formula 15}$$

wherein, $\phi_{Th}$ is a predetermined threshold, which can be set by the user autonomously. For example, the threshold can be set as 10, such: when the edge gradient standard deviation StdE is equal or above 10, it means there is almost no motion artefact in the image of the ROI, so the motion level factor $\phi$ may be 0; and if the edge gradient standard deviation StdE is below 10, it means there is motion artefact in the image of the ROI, and the more serious the motion artefact is, the greater the motion level factor $\phi$ is.

It should be understood that, there are lots of methods to calculate the motion level factor. In fact, any method can be used to calculate the motion level factor $\phi$ as long as it can reflect the seriousness of the motion artefact, and calculating the motion level factor $\phi$ by the edge gradient standard deviation StdE is described just as an example of the present disclosure.

Block 303: calculating motion amounts of the MVF corresponding to each of the time control points.

According to an example, calculating the motion amounts of the MVF corresponding to each of the time control points may comprise: calculating the derivatives of the project data corresponding to each of the time control points with respect to the MVF.

That is, after determining the ROI and the number of the time control points, the range of the projection data corresponding to each of the time control points can be determined according to the projection angle of the acquired projection data. Thus, the derivatives of the projection data corresponding to each of the time control points with respect to the MVF can be calculated by Formula 8 and Formula 9, i.e., the motion amounts of the MVF corresponding to each of the time control points without considering the direction and intensity of the motion.

Block 304: determining the direction of the MVF of the ROI.

According to an example, when determining the direction of the MVF of the ROI, many different directions can be applied to explore. Specifically, block 304 may comprise:

Block B1: setting several assumed directions;

In this example, because of the uncertainty of heart movement, the assumption of the direction of the MVF being in the X-axis positive direction and the Y-axis positive direction may be different from the practical case. In order to precisely estimate the direction of the practical heart motion of the scanned subject, motion direction factors of the X-axis and Y-axis $D_x, D_y$ are introduced to obtain 4 sets of the assumed directions: $D_x, D_y=\{(1,1),(-1,-1),(1,-1),(-1,1)\}$.

Block B2: calculating estimated MVFs in each of the assumed directions with the motion amounts of the MVFs corresponding to each of the time control points.

For example, the estimated MVFs in each of the assumed directions can be calculated through Formula 16 and Formula 17:

$$CD_{t_n,x}=c'_{t_n,x} \times D_x \qquad \text{Formula 16}$$

$$CD_{t_n,y}=c'_{t_n,y} \times D_y \qquad \text{Formula 17}$$

wherein, $D_x, D_y$ represent a set of assumed directions, $CD_{t_n,x}, CD_{t_n,y}$ represent the estimated motion vector corresponding to the time control point $t_n$ in the assumed directions, $c'_{t_n,x}, c'_{t_n,y}$ represent the motion amount of the MVFs corresponding to the time control point $t_n$.

Block B3: performing motion compensations on the ROI with the estimated MVF in each of the assumed directions, so as to reconstruct estimated images in each of the assumed directions;

With respect to the estimated MVFs in each of the assumed directions calculated in block B2, a filtered back projection based motion compensation algorithm may be applied to perform the motion compensation on the ROI, so as to reconstruct the estimated images in each of the assumed directions.

Block B4: calculating the edge gradient standard deviations of the estimated images in each of the assumed directions;

According to an example of the present disclosure, when calculating the edge gradient standard deviations of the estimated images, the similar methods with block A1 can be applied.

Block B5: comparing the edge gradient standard deviations corresponding to each of the assumed directions, and determining the assumed direction which corresponds to the maximum edge gradient standard deviation as the direction of the MVF of the ROI.

According to an example, as shown in FIG. 3, the process may proceed to block 305 after block 304: calculating the MVF of the ROI with the motion level factor, the motion amounts of the MVFs corresponding to each of the time control points and the direction of the MVF. For example. Formula 10 and Formula 11 can be directly adopted to calculate the MVF of the ROI.

In another example, after block 305, a motion compensated reconstruction can be performed on the projection data of the first reconstructed CT scan image by using the calculated MVF. That is, the method according to the disclosure may further comprise block 306, as follows: performing a motion compensation on the first reconstructed CT scan image by using the MVF of the ROI, so as to obtain a target reconstructed image with less motion artefacts.

In this example, the MVF calculated in block 305 is incorporated into the reconstruction, so as to obtain a target reconstructed image with motion compensation. The primary principle of the motion compensation is: with respect to the coordinates of a reconstructed point in each time control point, it can be corrected with the calculated MVF and then be used to reconstruct a corresponding motion compensated image.

Generally, there are two categories of reconstruction algorithm: filtered back projection based analytic reconstruction algorithm and algebraic reconstruction algorithm. For example, when adopting a filtered back projection based analytic reconstruction algorithm, the reconstructed CT scan image f(L) can be calculated through Formula 18:

$$f(L) = \sum_\beta p(\beta, B(\beta, x, y)) \qquad \text{Formula 18}$$

In this example, the filtered back projection based analytic reconstruction algorithm may be adopted as a basis of motion compensation algorithm (it should be understood that, other reconstruction algorithms such as an algebraic reconstruction algorithm and a perfect reconstruction algorithm may also be adopted), then Formula 18 is substituted with the MVF obtained in block 305 to form the following motion compensated reconstruction formula:

$$f(L) = \sum_\beta p(\beta, B(\beta, M(t_\beta, z, x, y, c_{t\beta,x,y}))) \qquad \text{Formula 19}$$

Obviously, Formula 19 is the same as Formula 1, wherein $M(t_\beta,z,x,y,c_{t\beta,x,y})$ are the coordinates value of the reconstructed point corrected by the MVF in time $t_\beta$, which can be calculated through Formula 3. Combining Formula 3 and Formula 19, it can be found that, the reconstructed coordinates in different time control point are shifted according to the MVF, and then the reconstruction result after motion compensation may be obtained.

Figure 4A:
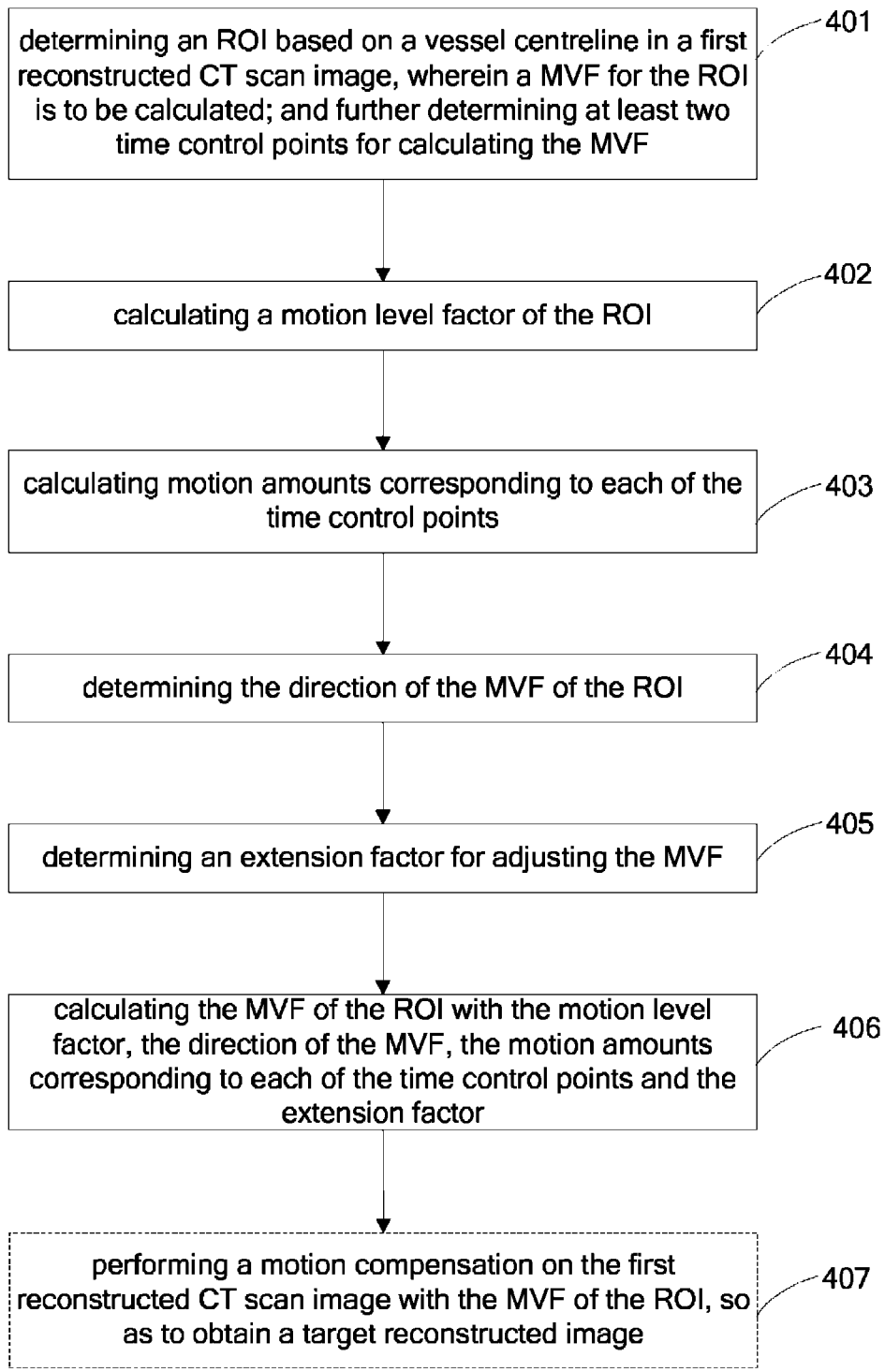
FIG. 4A is a schematic flowchart illustrating a method for calculating the MVF in a reconstructed CT scan image according to another example of the present disclosure.

For a better reconstruction result, an extension factor $\omega$ may be introduced to adjust the MVF. For example, FIG. 4A illustrates another example of the method for calculating the MVF in a reconstructed CT scan image. As shown in FIG. 4A, the method comprises:

Block 401: determining a ROI based on a vessel centreline in a first reconstructed CT scan image, wherein a MVF for the ROI is to be calculated; and further determining a time control points for calculating the MVF;

Block 402: calculating a motion level factor of the ROI;

Block 403: calculating motion amounts of the MVF corresponding to each of the time control points;

Block 404: determining the direction of the MVF of the ROI;

Block 405: determining an extension factor for adjusting the MVF;

According to an example of the present disclosure, when determining the extension factor, different extension factors can be applied to explore. Specifically, block 401 may comprise:

Block C1: calculating an initial MVF with the motion level factor, the motion amounts of the MVF corresponding to each of the time control points and the direction of the MVF.

Wherein, the method for calculating the initial MVF can be referred to the method for calculating the MVF of the ROI as shown in FIG. 3, i.e., Formula 10 and Formula 11 can be applied to calculate.

Block C2: setting several assumed extension factors with equal intervals, and calculating extended MVFs extended from the initial MVF by each of the assumed extension factors;

According to a specific example, 8 assumed extension factors may be set with an interval of 1, and thus 1, 2, 3, 4, 5, 6, 7, 8 may be obtained as the assumed extension factors. It should be understood that, the interval and the number of the assumed extension factors can be set according to practical application scenarios arbitrarily.

Besides, Formula 20 and Formula 21 can be applied to calculate the extended MVFs corresponding to each of the assumed extension factors:

$$C_{t_n,x,i} = \omega_i \times c_{t_n,x} \quad \text{Formula 20}$$

$$C_{t_n,y,i} = \omega_i \times c_{t_n,y} \quad \text{Formula 21}$$

Wherein, $\omega_i$ is the $i^{th}$ assumed extension factor, $C_{t_n,x,i}$, $C_{t_n,y,i}$ are the extended motion vectors extended by the $i^{th}$ assumed extension factor corresponding to the time control point $t_n$, and $c_{t_n,x}, c_{t_n,y}$ are the assumed motion vector corresponding to the time control point $t_n$. Obviously, Formula 20 and Formula 21 are substantially the same as Formula 12 and Formula 13. Comparing Formula 20 and Formula 21 with Formula 12 and Formula 13, it can be found that, extension factors are used for adjusting the MVF, so as to explore a relatively precise MVF, for a better reconstruction result.

Block C3: reconstructing extended images corresponding to each of the assumed extension factors by performing motion compensations on the ROI with each of the extended MVFs, and calculating the edge gradient standard deviations of each of the extended images;

With regard to the extended MVFs corresponding to each of the assumed extension factors calculated in block C2, a filtered back projection based motion compensation algorithm can be applied to perform a motion compensation on the ROI, so as to reconstruct extended images corresponding to each of the assumed extension factors.

Besides, when calculating the edge gradient standard deviations of each of the extended images, the similar method as introduced in block A1 can be applied.

Block C4: fitting a standard deviation variation curve based on each of the assumed extension factors and the edge gradient standard deviations corresponding to each of the assumed extension factors;

With the edge gradient standard deviation $E(\omega_i)$ corresponding to an assumed extension factor $\omega_i$, any skilled person in the art may apply any curve-fitting technology to fit a standard deviation variation curve $\epsilon(\omega)$ for illustrating the tendency for a extension factor with respect to the edge gradient standard deviations of the extended image corresponding to the extension factor. As shown in 4B, at first the edge gradient standard deviation $\epsilon(\omega)$ of the extended image increases with the increase of the extension factor $\omega$, and after reaching the peak, it decreases with the increase of the extension factor $\omega$.

Block C5: determining an extension factor which corresponds to the maximum edge gradient standard deviation along the standard deviation variation curve as the ultimate extension factor for the MVF.

Figure 4B:
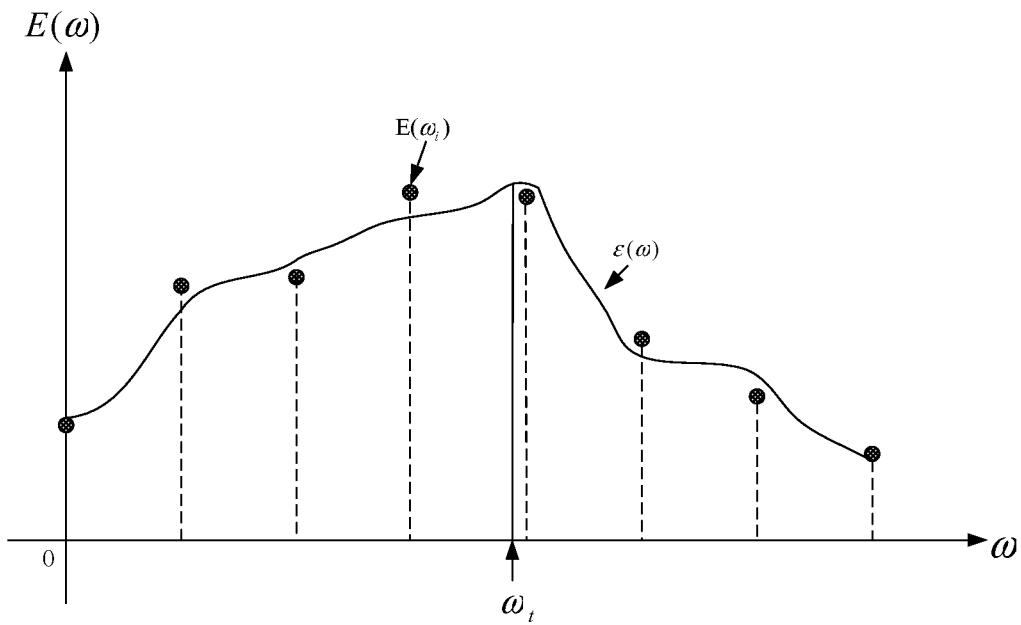
FIG. 4B schematically illustrates a fitting curve for variation of standard deviation.

As stated in the above, the higher the edge gradient standard deviation is, the sharper the edge of the image is, i.e., the less the motion artefact is. As shown in FIG. 4B, therefore, the extension factor corresponding to the peak value of the edge gradient standard deviation may be chosen as the ultimate extension factor $\omega_t$, that is, an adjusting factor of the MVF will be chosen in such a way that the motion artefact will be reduced to as minimum as possible.

On the premise of determining the ultimate extension factor $\omega_t$, the ultimate MVF should be considered with the ultimate extension factor $\omega_t$, i.e., the method may further comprise block 406: calculating the MVF of the ROI with the motion level factor, the motion amounts of the MVF corresponding to each of the time control points, the direction of the MVF and the extension factor.

According to an example, when calculating the ultimate MVF with considering the extension factor, Formula 12 and Formula 13 as stated in the above can be applied. It should be understood that, when block 405 is not executed, block 406 can be considered as block 305 in which the extension factor $\omega$ is of 1.

According to another example, after block 406, a motion compensation may be performed on the projection data of the first reconstructed CT scan image, i.e., the method may further comprises block 407. Meanwhile, since blocks 401~404 and 407 in FIG. 4A are essentially the same as blocks 301-304 and 306 in FIG. 3 respectively, repetition is omitted here.

As a summary, according to the present disclosure, first of all, it is assumed that there is a hypothetical motion in the first reconstructed heart CT scan image, and such motion is associated with time, for example, the projection data corresponding to the first reconstructed heart CT scan image are divided into ranges of different time control points, the derivatives of the projection data within each of the time control points with respect to the motion are respectively calculated as the motion amounts of the MVF corresponding to each of the time control points, different motion directions are applied to explore the direction of the MVF, and thus the MVF may be obtained directly according to the motion amounts of the MVF corresponding to each of the time control points and the direction of the MVF with low calculation complexity and high accuracy. Subsequently, a motion compensated reconstruction may be performed on the basis of the calculated MVF, so as to obtain a reconstructed image with higher time resolution and less motion artefacts.

Figure 5:
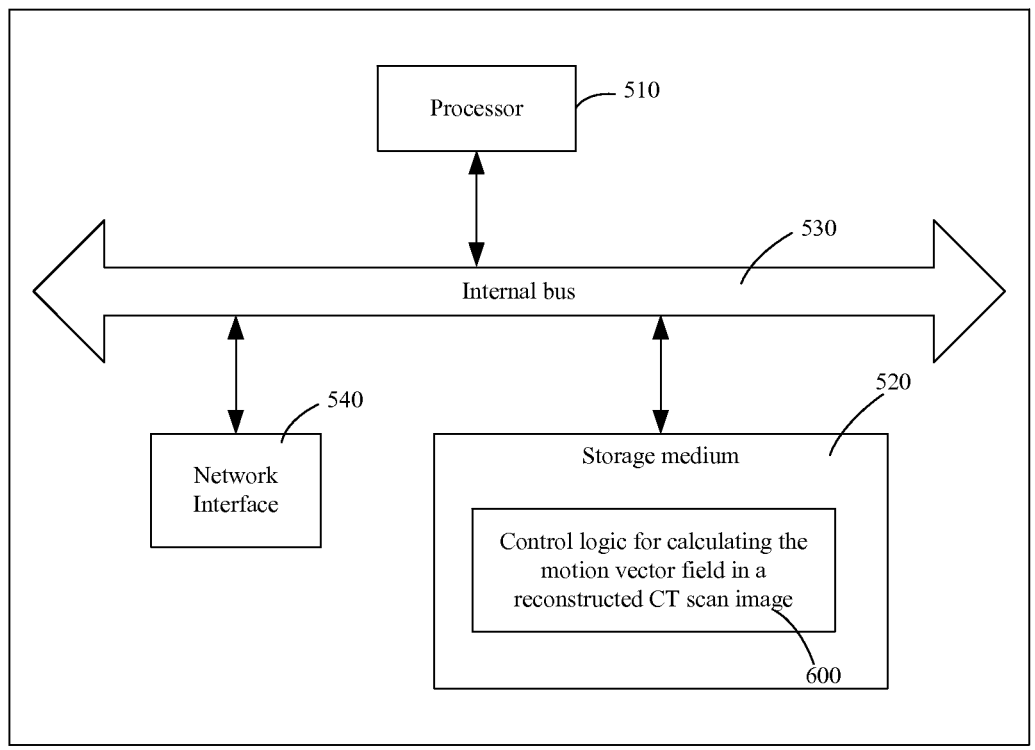
FIG. 5 schematically illustrates hardware structure of a device for calculating the MVF in a reconstructed CT scan image according to an example of the present disclosure.
Figure 6:
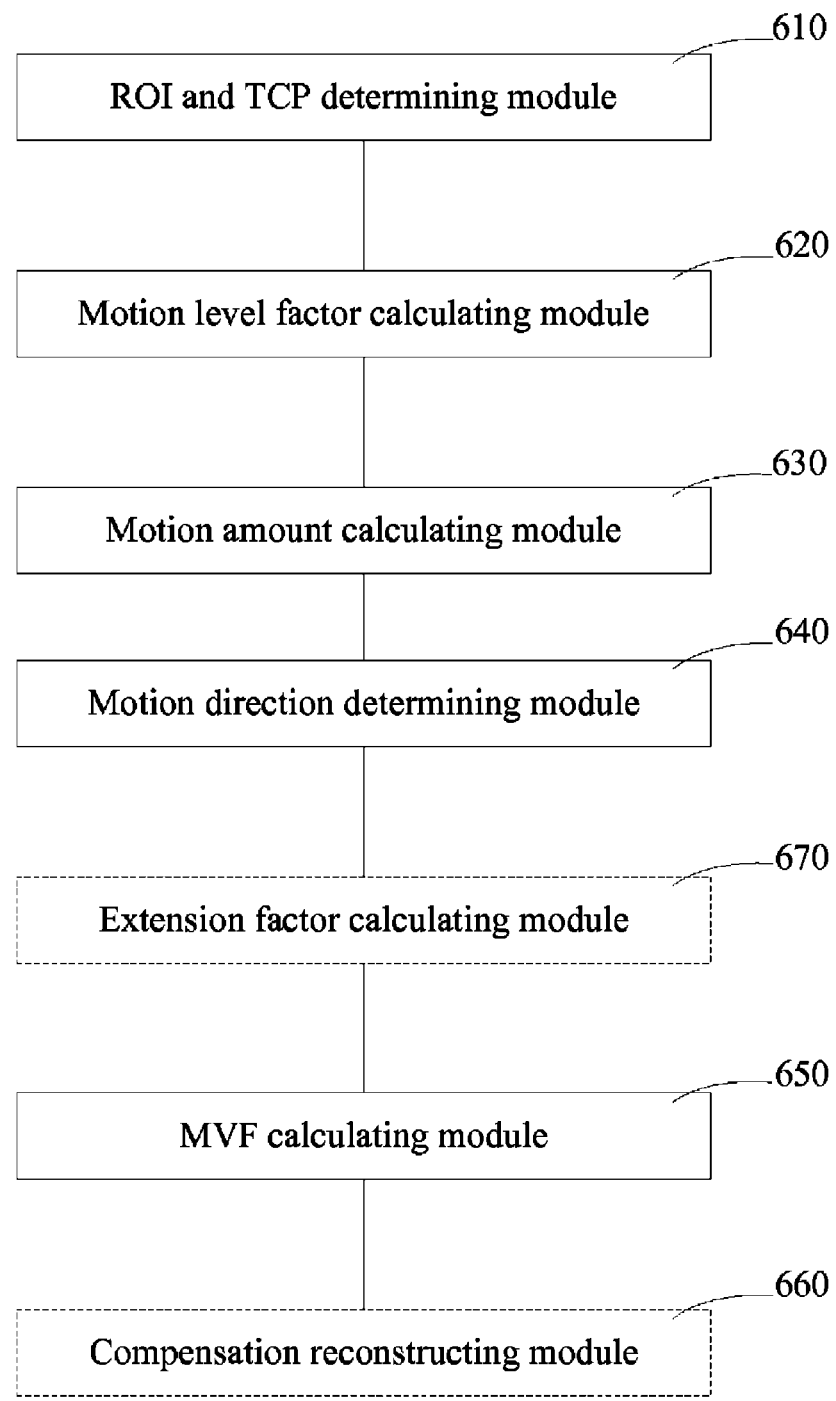
FIG. 6 schematically illustrates functional modules of a control logic for calculating the MVF in a reconstructed CT scan image according to an example of the present disclosure.

As shown in FIG. 5, the present disclosure provides a device for calculating the MVF in a reconstructed CT scan image. As shown in FIG. 5, the device may comprise a processor 510 such as CPU and a machine readable storage medium 520, wherein the processor 510 and the machine readable storage medium 520 are normally interconnected through an internal bus 530. In other potential examples, the device may further comprise an external interface 540, so as to communicate with other components or devices.

In different examples, the machine readable storage medium 520 may be: RAM (Random Access Memory), volatile memory, non-volatile memory, flash memory, storage device (such as hard disk drives), solid-state drives, any type of storage (such as CD-ROM DVD, etc), or the similar, or the combination thereof Furthermore, the machine readable storage medium 520 is stored with a control logic 600 for calculating the MVF in a reconstructed CT scan image. Functionally, the control logic 600 may comprise a ROI and TCP determining module 610, a motion level factor calculating module 620, a motion amount calculating module 630, a motion direction determining module 640 and a MVF calculating module 650.

The ROI and TCP determining module 610 may determine a region of interest (ROI) a vessel centreline in a first reconstructed CT scan image, wherein a motion vector field (MVF) for the ROI is to be calculated. And the ROI and TCP determining module 610 may further determine a time control points for calculating the MVF of the ROI.

The motion level factor calculating module 620 may calculate a motion level factor of the ROI.

Wherein, the motion level factor calculating module 620 may further comprise: a standard deviation calculating submodule, for calculating the edge gradient standard deviation of the ROI; and a level factor determining sub-module, for determining the motion level factor based on the edge gradient standard deviation and a preset threshold.

The motion amount calculating module 630 may calculate motion amounts of the MVF corresponding to each of the time control points. Wherein, the motion amount calculating module 630 may further comprise: a derivative calculating submodule, for calculating the derivatives of the projection data corresponding to each of the time control points with respect to the MVF. The formulas for calculating the derivatives may refer to Formula 8 and Formula 9 as stated in the above;

The motion direction determining module 640 may determine the direction of the MVF of the ROI. Wherein, the motion direction determining module 640 may further comprise: a setting sub-module, for setting several assumed directions; a vector field calculating sub-module, for calculating estimated MVFs in each of the assumed directions with the motion amounts of the MVF corresponding to each of the time control points; a compensation reconstructing sub-module, for performing motion compensations on the ROI with the estimated MVFs in each of the assumed directions, so as to reconstruct estimated images in each of the assumed directions; a standard deviation calculating sub-module, for calculating the edge gradient standard deviations of the estimated images in each of the assumed directions; and a direction determining sub-module, for comparing the edge gradient standard deviations corresponding to each of the assumed directions, and determining the assumed direction which corresponds to the maximum edge gradient standard deviation as the direction of the MVF of the ROI.

The MVF calculating module 650 may calculate the MVF of the ROI with the motion level factor, the motion amounts of the MVF corresponding to each of the time control points and the direction of the MVF.

According to another example of the present disclosure, functionally, the control logic 600 may further comprise a compensation reconstructing module 660. The compensation reconstructing module 660 may perform a motion compensation on the first reconstructed CT scan image based on the MVF of the ROI, so as to obtain the target reconstructed image which has been motion compensated.

According to another example of the present disclosure, functionally, the control logic 600 may further comprise an extension factor calculating module 670. The extension factor calculating module 670 may calculate an extension factor for adjusting the MVF when the direction of the MVF is determined.

The extension factor calculating module 670 may further comprise: an initial MVF calculating sub-module, for calculating an initial MVF with the motion level factor, the motion amounts of the MVF corresponding to each of the time control points and the direction of the MVF; a setting sub-module, for setting several assumed extension factors with equal intervals, and calculating extended MVFs extended from the initial MVF by each of the assumed extension factors; a standard deviation calculating sub-module, for reconstructing extended images corresponding to each of the assumed extension factors by performing motion compensations on the ROI with each of the extended MVFs, and calculating the edge gradient standard deviation of each of the extended images; a curve fitting sub-module, for fitting a standard deviation variation curve according to each of the assumed extension factors and the edge gradient standard deviations corresponding to each of the assumed extension factors; and an extension factor determining sub-module, for determining an extension factor which corresponds to the maximum edge gradient standard deviation along the standard deviation variation curve as the ultimate extension factor for the MVF.

In this case, the MVF calculating module 650 may calculate the MVF of the ROI according to the motion level factor, the motion amounts of the MVF corresponding to each of the time control points, the direction of the MVF and the extension factor.

The present disclosure will take software implementation as an example to illustrate how a device calculate the MVF in a reconstructed CT scan image according to the control logic 600. In the example, the control logic 600 should be understood as machine readable instructions stored in the machine readable storage medium 520. When the processor 510 executes the control logic 600, the processor 510 invokes the instructions corresponding to the control logic 600 stored on the machine readable storage medium 520 to:

determine a region of interest (ROI) based on a vessel centreline in a first reconstructed CT scan image, wherein a motion vector field (MVF) for the ROI is to be calculated;

determine a control point for calculating the MVF;

calculate a motion level factor of the ROI;

calculate motion amounts of the MVF corresponding to each of the time control points;

determine the direction of the MVF of the ROI; and calculate the MVF of the ROI according to the motion level factor, the motion amounts of the MVF corresponding to each of the time control points and the direction of the MVF.

In an example, the processor 510 further invokes the machine readable instructions to: determine an extension factor for adjusting the MVF when the direction of the MVF of the ROI is determined.

In this case, the processor 510 may further calculate the MVF of the ROI according to the motion level factor, the motion amounts of the MVF corresponding to each of the time control points, the direction of the MVF and the extension factor. Wherein the formula for calculating the MVF of the ROI according to the motion level factor, the motion amounts of the MVF corresponding to each of the time control points, the direction of the MVF and the extension factor may be:

$$C_{t_n,x} = \omega \times c_{t_n,x} = \omega \times \eta \times c'_{t_n,x},$$

$$C_{t_n,y} = \omega \times c_{t_n,y} = \omega \times \eta \times \phi \times c'_{t_n,y},$$

wherein, $c'_{t_n,x}, c'_{t_n,y}$ are the motion amounts of the MVF corresponding to the time control points $t_n$, $C_{t_n,x}, C_{t_n,y}$ are the motion vectors corresponding to the time control points $t_n$, and the MVF of the ROI comprises the motion vectors corresponding to each of the time control points, ω is the extension factor, η is the direction of the MVF, φ is the motion level factor.

For determining the extension factor, the processor 510 may further invoke the machine readable instructions to:

calculate an initial MVF according to the motion level factor, the motion amounts of the MVF corresponding to each of the time control points and the direction of the MVF;

set several assumed extension factors with equal intervals, and calculate extended MVFs extended from the initial MVF by each of the assumed extension factors;

reconstruct extended images corresponding to each of the assumed extension factors by performing motion compensations on the ROI with each of the extended MVFs, and calculate the edge gradient standard deviations of each of the extended images;

fitting a standard deviation variation curve based on each of the assumed extension factors and the edge gradient standard deviations corresponding to each of the assumed extension factors; and determine an assumed extension factor which corresponds to the maximum edge gradient standard deviation along the standard deviation variation curve as the extension factor.

For determining the motion level factor, the processor 510 further invokes the machine readable instructions to:

calculate the edge gradient standard deviation of the ROI; and determine the motion level factor based on the edge gradient standard deviation and a preset threshold.

Wherein the edge gradient standard deviation of the ROI is calculated based on the absolute value of the edge gradient, and a formula for calculating the absolute value of edge gradient of the ROI may be as follows:

$$E(a,b) = \frac{|f(a,b) - f(a+1,b)|}{\Delta x} + \frac{|f(a,b) - f(a,b+1)|}{\Delta y}$$

Wherein, E(a,b) is the absolute value of the edge gradient on the pixel (a,b);

$\Delta x$ is the pixel sampling interval on the X-axis, and $\Delta y$ is the pixel sampling interval on the Y-axis;

a is the X-axis index of the pixel (a,b), and b is the Y-axis index of the pixel (a,b); and f(a,b) is the value of the pixel (a,b) on the reconstructed image of the ROI.

Further, a formula for determining the motion level factor based on the edge gradient standard deviation and the preset threshold may be:

$$\varphi = \begin{cases} 0 & StdE \geq \varphi_{Th} \\ \varphi_{Th} - StdE & StdE < \varphi_{Th} \end{cases}$$

wherein, $\varphi_{Th}$ is the preset threshold, StdE is the edge gradient standard deviation, and $\varphi$ is the motion level factor.

For calculating the motion amounts of the MVF corresponding to each of the time control points, the processor 510 further invokes the machine readable instructions to:

determine the range of the projection data corresponding to each of the time control points based on the projection angle for acquiring the projection data;

calculate the derivatives of the projection data corresponding to each of the time control points with respect to the MVF as the motion amount of the MVF corresponding to each of the time control point, by the following formula:

$$c'_{t_n,x} = \frac{\partial \overline{\tau}}{\partial x_{t_n}} = \sum_{t_\beta \in t_n} \left( \frac{\partial p}{\partial u} \frac{\partial u}{\partial x} + \frac{\partial p}{\partial v} \frac{\partial v}{\partial x} \right) \times \frac{\partial M(t_\beta, x, y, c_{t_\beta,x,y})}{\partial x},$$

$$c'_{t_n,y} = \frac{\partial \overline{\tau}}{\partial y_{t_n}} = \sum_{t_\beta \in t_n} \left( \frac{\partial p}{\partial u} \frac{\partial u}{\partial y} + \frac{\partial p}{\partial v} \frac{\partial v}{\partial y} \right) \times \frac{\partial M(t_\beta, x, y, c_{t_\beta,x,y})}{\partial y},$$

wherein, $\vec{\tau}$ is the MVF, x,y are coordinates of a reconstructed point on the reconstructed CT scan image f(L), β is the projection angle, $t_\beta$ is the collecting time of the projection data of the projection angle β, and the collecting time $t_\beta$ is within the range of the time control point $t_n$, p is the projection data, u,v are parameters regarding channel and slice direction of the detector, $M(t,x,y,c_{t,x,y})$ are corrected coordinates of the reconstructed point, $c_{t,x}$ is the X-axis projection value of the motion vector at time t, and $c_{t,y}$ is the Y-axis projection value of the motion vector at time t, $c'_{t_n,x}, c'_{t_n,y}$ are the motion amount of the MVF corresponding to the time control point $t_n$.

For determining the direction of the MVF, the processor 510 may further invoke the machine readable instructions to:

set multiple assumed directions;

calculate estimated MVFs in each of the assumed directions with the motion amounts of the MVF corresponding to each of the time control points; and perform motion compensations on the ROI with the estimated MVFs in each of the assumed directions, so as to reconstruct estimated images on each of the assumed directions;

calculate the edge gradient standard deviations of each of the estimated images; and determine the assumed direction which corresponds to the maximum edge gradient standard deviation among the present edge gradient standard deviations of each of the estimated images, as the direction of the MVF of the ROI.

The above are only preferred examples of the present disclosure is not intended to limit the disclosure within the spirit and principles of the present disclosure, any changes made, equivalent replacement, or improvement in the protection of the present disclosure should contain within the range.

The methods, processes and units described herein may be implemented by hardware (including hardware logic circuitry), software or firmware or a combination thereof. The term 'processor' is to be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

Further, the processes, methods and functional units described in this disclosure may be implemented in the form of a computer software product. The computer software product is stored in a storage medium and comprises a plurality of instructions for making a processor to implement the methods recited in the examples of the present disclosure.

The figures are only illustrations of an example, wherein the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for calculating the motion vector field (MVF) in a reconstructed Computed Tomography (CT) scan image, comprises:
   determining a region of interest (ROI) based on a vessel centreline in a first reconstructed CT scan image, wherein a motion vector field (MVF) for the ROI is to be calculated;
   determining time control points for calculating the MVF;
   calculating a motion level factor of the ROI;
   calculating motion amounts of the MVF corresponding to each of the time control points;
   determining the direction of the MVF of the ROI;
   calculating the MVF of the ROI according to the motion level factor, the motion amounts of the MVF corresponding to each of the time control points and the direction of the MVF; and
   reconstructing a target reconstructed image by performing a motion compensation on the first reconstructed CT scan image according to the MVF of the ROI.

2. The method of claim 1, further comprises:
   determining an extension factor for adjusting the MVF after the direction of the MVF is determined; and then
   calculating the MVF of the ROI according to the motion level factor, the motion amounts of the MVF corresponding to each of the time control points, the direction of the MVF and the extension factor.

3. The method of claim 2, wherein, a formula for calculating the MVF of the ROI according to the motion level factor, the motion amounts of the MVF corresponding to each of the time control points, the direction of the MVF and the extension factor is as following:

$$C_{t_n,x} = \omega \times c_{t_n,x} = \omega \times \eta \times \phi \times c'_{t_n,x},$$

$$C_{t_n,y} = \omega \times c_{t_n,y} = \omega \times \eta \times \phi \times c'_{t_n,y},$$

wherein, $c'_{t_n,x}, c'_{t_n,y}$ are the motion amounts of the MVF corresponding to the time control points $t_n$,
$C_{t_n,x}, C_{t_n,y}$ are the motion vector corresponding to the time control points $t_n$, and the MVF of the ROI comprises the motion vectors corresponding to each of the time control points,
ω is the extension factor,
η is the direction of the MVF, and
ϕ is the motion level factor.

4. The method of claim 2, wherein, determining the extension factor for adjusting the MVF comprises:
   calculating an initial MVF according to the motion level factor, the motion amounts of the MVF corresponding to each of the time control points and the direction of the MVF;
   setting at least two assumed extension factor with equal intervals, and calculating extended MVFs extended from the initial MVF by each of the assumed extension factors;
   reconstructing extended images corresponding to each of the assumed extension factors by performing motion compensations on the ROI with each of the extended MVFs, and calculating the edge gradient standard deviations of each of the extended images;
   fitting a standard deviation variation curve based on each of the assumed extension factors and the edge gradient standard deviations corresponding to each of the assumed extension factors; and
   determining an extension factor which corresponds to the maximum edge gradient standard deviation along the standard deviation variation curve as the extension factor.

5. The method of claim 1, wherein, calculating the motion level factor of the ROI comprises:
   calculating the edge gradient standard deviation of the ROI; and
   determining the motion level factor based on the edge gradient standard deviation and a preset threshold.

6. The method of claim 5, wherein, the edge gradient standard deviation of the ROI is calculated based on the absolute value of the edge gradient, and a formula for calculating the absolute value of the edge gradient of the ROI is as follows:

$$E(a,b) = \frac{|f(a,b) - f(a+1,b)|}{\Delta x} + \frac{|f(a,b) - f(a,b+1)|}{\Delta y}$$

wherein, E(a,b) is the absolute value of the edge gradient on the pixel (a,b);
Δx is the pixel sampling interval on the X-axis, and Δy is the pixel sampling interval on the Y-axis;
a is the X-axis index of the pixel (a,b), and b is the Y-axis index of the pixel (a,b); and
f(a,b) is the value of the pixel (a,b) on the image of the ROI.

7. The method of claim 4, wherein, a formula for determining the motion level factor based on the edge gradient standard deviation and the preset threshold is:

$$\varphi = \begin{cases} 0 & StdE \geq \varphi_{Th} \\ \varphi_{Th} - StdE & StdE < \varphi_{Th} \end{cases}$$

wherein, $\phi_{Th}$ is the preset threshold, StdE is the edge gradient standard deviation, and ϕ is the motion level factor.

8. The method of claim 1, wherein, calculating the motion amounts of the MVF corresponding to each of the time control points comprises:
   determining the range of the projection data corresponding to each of the time control points based on the projection angle for acquiring the projection data;
   calculating the derivatives of the projection data corresponding to each of the time control points with respect to the MVF as the motion amount of the MVF corresponding to each of the time control point, by the following formula:

$$c'_{t_n,x} = \frac{\partial \overline{\tau}}{\partial x_{t_n}} = \sum_{t_\beta \in t_n} \left( \frac{\partial p}{\partial u} \frac{\partial u}{\partial x} + \frac{\partial p}{\partial v} \frac{\partial v}{\partial x} \right) \times \frac{\partial M(t_\beta, x, y, c_{t_\beta,x,y})}{\partial x},$$

$$c'_{t_n,y} = \frac{\partial \overline{\tau}}{\partial y_{t_n}} = \sum_{t_\beta \in t_n} \left( \frac{\partial p}{\partial u} \frac{\partial u}{\partial y} + \frac{\partial p}{\partial v} \frac{\partial v}{\partial y} \right) \times \frac{\partial M(t_\beta, x, y, c_{t_\beta,x,y})}{\partial y},$$

wherein, $\vec{\tau}$ is the MVF, x,y are coordinates of a reconstructed point on the reconstructed CT scan image f(L), $\beta$ is the projection angle, $t_\beta$ is the collecting time of the projection data of the projection angle $\beta$, and the collecting time $t_\beta$ is within the range of the time control point $t_n$, p is the projection data, u,v are parameters regarding channel and slice direction of the detector, $M(t,x,y,c_{t,x,y})$ is corrected coordinates of the reconstructed point, $c_{t,x}$ is the X-axis projection value of the motion vector at time t, and $c_{t,y}$ is the Y-axis projection value of the motion vector at time t, and $c'_{t_n,x}, c'_{t_n,y}$ are the motion amount of the MVF corresponding to the time control point $t_n$.

9. The method of claim 1, wherein, determining the direction of the MVF of the ROI comprises:

setting at least two assumed directions;

calculating estimated MVFs in each of the assumed directions with the motion amounts of the MVF corresponding to each of the time control points;

performing motion compensations on the ROI with the estimated MVFs in each of the assumed directions, so as to reconstruct estimated images in each of the assumed directions;

calculating the edge gradient standard deviations of each of the estimated images; and determining the assumed direction which corresponds to the maximum edge gradient standard deviation among the edge gradient standard deviations of each of the estimated images, as the direction of the MVF of the ROI.

10. A device for calculating the motion vector field (MVF) in a reconstructed Computed Tomography (CT) scan image, the device comprises a processor which invokes machine readable instructions corresponding to a control logic for calculating a MVF in a reconstructed CT scan image stored on a storage medium and executes the machine readable instructions to:

determine a region of interest (ROI) based on a vessel centreline in a first reconstructed CT scan image, wherein a motion vector field (MVF) for the ROI is to be calculated;

determine at least two time control points for calculating the MVF;

calculate a motion level factor of the ROI;

calculate motion amounts of the MVF corresponding to each of the time control points;

determine the direction of the MVF of the ROI;

calculate the MVF of the ROI according to the motion level factor, the motion amounts of the MVF corresponding to each of the time control points and the direction of the MVF; and reconstruct a target reconstructed image by performing a motion compensation on the first reconstructed CT scan image according to the MVF of the ROI.

11. The device according to claim 10, wherein said machine readable instructions further cause the processor to:

determine an extension factor for adjusting the MVF after the direction of the MVF is determined; and then calculate the MVF of the ROI according to the motion level factor, the motion amounts of the MVF corresponding to each of the time control points, the direction of the MVF and the extension factor.

12. The device according to claim 11, wherein a formula for calculating the MVF of the ROI according to the motion level factor, the motion amounts of the MVF corresponding to each of the time control points, the direction of the MVF and the extension factor is as following:

$$C_{t_n,x} = \omega \times c_{t_n,x} = \omega \times \eta \times \phi \times c'_{t_n,x},$$

$$C_{t_n,y} = \omega \times c_{t_n,y} = \omega \times \eta \times \phi \times c'_{t_n,y},$$

wherein, $c'_{t_n,x}, c'_{t_n,y}$ are the motion amounts of the MVF corresponding to the time control point $t_n$, $C_{t_n,x}, C_{t_n,y}$ are the motion vectors corresponding to the time control point $t_n$, and the MVF of the ROI comprises the motion vectors corresponding to each of the time control points, $\omega$ is the extension factor, $\eta$ is the direction of the MVF, and $\phi$ is the motion level factor.

13. The device according to claim 11, wherein said machine readable instructions further cause the processor to:

calculate an initial MVF according to the motion level factor, the motion amounts of the MVF corresponding to each of the time control points and the direction of the MVF;

set at least two assumed extension factors with equal intervals;

calculate extended MVFs extended from the initial MVF by each of the assumed extension factors;

reconstruct extended images corresponding to each of the assumed extension factors by performing motion compensations on the ROI with each of the extended MVFs;

calculate the edge gradient standard deviations of each of the extended images;

fit a standard deviation variation curve based on each of the assumed extension factors and the edge gradient standard deviations corresponding to each of the assumed extension factors; and determine an extension factor which corresponds to the maximum edge gradient standard deviation along the standard deviation variation curve as the extension factor.

14. The device according to claim 10, wherein said machine readable instructions further cause the processor to:

calculate the edge gradient standard deviation of the ROI; and determine the motion level factor based on the edge gradient standard deviation and a preset threshold.

15. The device according to claim 14, wherein the edge gradient standard deviation of the ROI is calculated based on the absolute value of the edge gradient, and a formula for calculating the absolute value of the edge gradient of the ROI is as follows:

$$E(a,b) = \frac{|f(a,b) - f(a+1,b)|}{\Delta x} + \frac{|f(a,b) - f(a,b+1)|}{\Delta y}$$

wherein, E(a,b) is the absolute value of the edge gradient on the pixel (a,b);

Δx is the pixel sampling interval on the X-axis, and Δy is the pixel sampling interval on the Y-axis;
a is the X-axis index of the pixel (a,b), and b is the Y-axis index of the pixel (a,b); and
f(a,b) is the value of the pixel (a,b) on the image of the ROI.

16. The device according to claim 14, wherein a formula for determining the motion level factor based on the edge gradient standard deviation and the preset threshold is:

$$\varphi = \begin{cases} 0 & StdE \geq \varphi_{Th} \\ \varphi_{Th} - StdE & StdE < \varphi_{Th} \end{cases}$$

wherein, $\phi_{Th}$, is the preset threshold, StdE is the edge gradient standard deviation, and $\phi$ is the motion level factor.

17. The device according to claim 10, wherein said machine readable instructions further cause the processor to:
determine the range of the projection data corresponding to each of the time control points based on the projection angle for acquiring the projection data;
calculate the derivatives of the projection data corresponding to each of the time control points with respect to the MVF as the motion amount of the MVF corresponding to each of the time control points, by the following formula:

$$c'_{t_n,x} = \frac{\partial \vec{\tau}}{\partial x_{t_n}} = \sum_{t_\beta \in t_n} \left( \frac{\partial p}{\partial u} \frac{\partial u}{\partial x} + \frac{\partial p}{\partial v} \frac{\partial v}{\partial x} \right) \times \frac{\partial M(t_\beta, x, y, c_{t_\beta, x, y})}{\partial x},$$

$$c'_{t_n,y} = \frac{\partial \vec{\tau}}{\partial y_{t_n}} = \sum_{t_\beta \in t_n} \left( \frac{\partial p}{\partial u} \frac{\partial u}{\partial y} + \frac{\partial p}{\partial v} \frac{\partial v}{\partial y} \right) \times \frac{\partial M(t_\beta, x, y, c_{t_\beta, x, y})}{\partial y},$$

wherein, $\vec{\tau}$ is the MVF,
x,y are coordinates of a reconstructed point on the reconstructed CT scan image f(L),
β is the projection angle,
$t_\beta$ is the collecting time of the projection data of the projection angle β, and the collecting time $t_\beta$ is within the range of the time control point $t_n$,
p is the projection data,
u,v are parameters regarding channel and slice direction of the detector,
$M(t,x,y,c_{t,x,y})$ are corrected coordinates of the reconstructed point, $c_{t,x}$ is the X-axis projection value of the motion vector at time t, and $c_{t,y}$ is the Y-axis projection value of the motion vector at time t, and
$c'_{t_n,x}, c'_{t_n,y}$ are the motion amount of the MVF corresponding to the time control point $t_n$.

18. The device according to claim 10, wherein said machine readable instructions further cause the processor to:
set at least two assumed directions;
calculate estimated MVFs in each of the assumed directions with the motion amounts of the MVF corresponding to each of the time control points;
perform motion compensations on the ROI with the estimated MVFs in each of the assumed directions, so as to reconstruct estimated images on each of the assumed directions;
calculate the edge gradient standard deviations of each of the estimated images; and
determine the assumed direction which corresponds to the maximum edge gradient standard deviation among the present edge gradient standard deviations of each of the estimated images, as the direction of the MVF of the ROI.

* * * * *